US012661413B2

(12) United States Patent

Yeh

(10) Patent No.: US 12,661,413 B2

(45) Date of Patent: Jun. 23, 2026

(54) METHOD AND MATERIAL TO ACQUIRE MAGNETIC RESONANCE IMAGING DATA

(71) Applicants: THE REGENTS OF THE UNIVERSITY OF CALIFORNIA, Oakland, CA (US); THE UNITED STATES GOVERNMENT, as represented by THE DEPARTMENT OF VETERANS AFFAIRS, Washington, DC (US)

(72) Inventor: Benjamin M. Yeh, Hillsborough, CA (US)

(73) Assignees: The Regents of the University of California, Oakland, CA (US); The United States Government, as represented by The Department of Veterans Affairs, Washington, DC (US)

( * ) Notice: Subject to any disclaimer, the term of this patent is extended or adjusted under 35 U.S.C. 154(b) by 591 days.

(21) Appl. No.: 17/266,525

(22) PCT Filed: Aug. 9, 2019

(86) PCT No.: PCT/US2019/046022

§ 371 (c)(1),
(2) Date: Feb. 5, 2021

(87) PCT Pub. No.: WO2020/033904

PCT Pub. Date: Feb. 13, 2020

(65) Prior Publication Data

US 2021/0299284 A1 Sep. 30, 2021

Related U.S. Application Data

(60) Provisional application No. 62/716,500, filed on Aug. 9, 2018.

(51) Int. Cl.
| | | |
|---|---|---|
| *A61K 49/18* | (2006.01) | |
| *A61B 5/00* | (2006.01) | |

(Continued)

(52) U.S. Cl.
CPC .......... *A61K 49/1818* (2013.01); *A61B 5/004* (2013.01); *A61B 5/055* (2013.01);

(Continued)

(58) Field of Classification Search
None
See application file for complete search history.

(56) References Cited

U.S. PATENT DOCUMENTS

| | | | | |
|---|---|---|---|---|
| 5,120,527 A | * | 6/1992 | Li | ...................... A61K 49/1806 514/975 |
| 5,792,445 A | | 8/1998 | Tournier et al. | |

(Continued)

FOREIGN PATENT DOCUMENTS

| | | |
|---|---|---|
| JP | 2009-510204 | 10/1997 |
| JP | 2018-513837 | 5/2018 |

(Continued)

OTHER PUBLICATIONS

Kwiatkowski et al., "Nanometer size silicon particles for hyperpolarized MRI". Scientific Reports, 7 (2017): pp. 1-6. (Year: 2017).*

(Continued)

*Primary Examiner* — Yi-Shan Yang

(74) *Attorney, Agent, or Firm* — Morgan, Lewis & Bockius LLP

(57) ABSTRACT

Provided are MR images of a subject gastrointestinal tract structure in which the lumen of the structure is usefully darkened on both T1-weighted and T2-weighted images when the structure is imaged following administration to the subject of an enteric contrast agent formulation with particles containing encapsulated gas or partial vacuum. The (Continued)

Pre-ingestion    30 min post-ingestion

A    B present invention provides an encapsulated gas or partial vacuum particle contrast medium of use in acquiring such MR images. In an exemplary embodiment, the invention provides an enteric contrast medium formulation. An exemplary formulation comprises, (a) an enteric contrast medium comprising a encapsulated gas or partial vacuum particle suspended in water.

31 Claims, 11 Drawing Sheets

(51) Int. Cl.
      *A61B 5/055*      (2006.01)
      *A61K 9/00*       (2006.01)
      *A61K 47/36*      (2006.01)
(52) U.S. Cl.
      CPC .......... *A61B 5/4238* (2013.01); *A61B 5/4255* (2013.01); *A61K 9/0053* (2013.01); *A61K 47/36* (2013.01)

(56) References Cited

U.S. PATENT DOCUMENTS

| | | | | |
|---|---|---|---|---|
| 5,795,562 A | * | 8/1998 | Klaveness | A61K 49/223 |
| | | | | 424/9.52 |
| 5,922,304 A | * | 7/1999 | Unger | A61K 47/6925 |
| | | | | 424/9.3 |
| 6,117,414 A | | 9/2000 | Unger | |
| 6,136,292 A | * | 10/2000 | Pettersson | A61K 49/1887 |
| | | | | 424/9.322 |
| 2002/0065467 A1 | * | 5/2002 | Schutt | A61K 49/223 |
| | | | | 600/458 |
| 2005/0271591 A1 | | 12/2005 | Walovitch et al. | |
| 2017/0007148 A1 | * | 1/2017 | Kaditz | A61B 5/055 |
| 2020/0179539 A1 | * | 6/2020 | Lewis | A61K 49/0428 |

FOREIGN PATENT DOCUMENTS

| | | |
|---|---|---|
| WO | WO 1995/020405 | 8/1995 |
| WO | WO 1995/024184 | 9/1995 |
| WO | WO 2016/172256 | 10/2016 |
| WO | WO-2016172256 A1 * 10/2016 | ............... A61B 6/03 |

OTHER PUBLICATIONS

International Search Report and Written Opinion for PCT/US2019/046022 dated Oct. 8, 2019, 12 pages.

European Extended Search Report for PCT/US2019/046022 dated Apr. 5, 2022, 8 pages.

Ueguchi et al., Air Microbubbles as MR Susceptibility Contrast Agent at 1.5 Tesla, Magnetic Resonance In Medical Sciences, vol. 5, No. 3, 2006, pp. 147-150.

Cheung et al. (2009) "Microbubbles as novel contrast agent for brain MRI," NeuroImage, 46:3, 658-664.

* cited by examiner

A

B

A

B

C

D

A

B

C

D

A

B

C

D

Pre-ingestion            30 min post-ingestion            60 min post-ingestion

A                        B                                C

Pre-ingestion          30 min post-ingestion          60 min post-ingestion

A                      B                              C

METHOD AND MATERIAL TO ACQUIRE MAGNETIC RESONANCE IMAGING DATA

CROSS REFERENCE TO RELATED APPLICATIONS

This application claims priority to U.S. Provisional Patent Application No. 62/716,500 filed Aug. 9, 2018, all of which is expressly incorporated herein by reference in its entirety.

BACKGROUND OF THE INVENTION

The acquisition of medical magnetic resonance (MR) images using enteric contrast media is valuable for many clinical scenarios, including to assess a subject for bowel tumors and inflammation, implants and endometriosis, or to better delineate extra-enteric disease. The native bowel appearance is highly variable. For example, the bowel may be distended or non-distended at the time of MR imaging. When the bowel is imaged in the non-distended state, it is common to be unable to exclude the diagnosis of bowel wall thickening from inflammation or tumor. Similarly, the MR signal in bowel lumen in various segments of the bowel may be bright or neutral or dark on both T1-weighted and T2-weighted images, even within the same MR scan, and hence be distracting or confusing during image interpretation since many diseases and lesions in and around the bowel appear as areas of neutral or bright signal on T1- and T2-weighted images. To help resolve these issues, enteric contrast may be administered into the bowel by mouth or through a tube in order to distend the bowel, ideally with material that has a different MR signal than that of bowel wall or intravenous contrast material.

The native bowel lumen usually contains fluid and gas. Native bowel lumen fluid generally has low signal on T1- and high signal on T2-weighted images. Such fluid may mask bowel wall edema on T2-weighed images since fluid in the bowel lumen and fluid in the bowel wall may show similar signal. Native bowel gas generally has low signal on both T1- and T2-weighted images. However, since collections of native bowel gas are often fairly large in size (>5 mm), such intralumenal bowel gas collections may cause surrounding low signal artifacts that interfere with local anatomic detail, especially on T2-weighted fat saturation images and T1-weighted gradient echo sequences that are critical for imaging of intravenous contrast material enhancement of the bowel wall. Furthermore, the presence of alternating areas of fluid and gas within bowel wall segments may cause confusing alternating areas of bright and dark signal, respectively, on T2-weighted images. On T1-weighted images, native bowel contents, particularly in the ileum and colon, may be very bright in signal and thus interfere with the ability to assess for enhancement of the bowel wall with intravenous gadolinium contrast agents at T1-weighted images. A more homogeneous signal throughout the bowel lumen would reduce confusion.

Medical MR images acquired using contrast material for the bowel may be bright, or "positive," and give high signal that is substantially greater than tissue using either T1- or T2-weighted sequences. Contrast agents giving bright signal on T1-weighted images include agents with dilute concentrations of T1 shortening materials such as gadolinium, manganese, or iron. These latter agents may give a range of possible signals on T2-weighted images, including bright, neutral, or dark contrast, depending on the concentration of the T1-shortening material, with low concentrations giving bright, and high concentrations of material often giving dark signal on T2-weighted images. Excessively high concentrations may also cause image artifacts on nearby anatomic structures. This variability in signal of such contrast material is generally undesirable and may cause diagnostic ambiguity.

Enteric contrast agents giving bright signal on T2-weighted images include water-based agents that do not contain materials causing substantial susceptibility artifact. Such agents include most beverages or low-concentration oral barium products. Such agents are termed "biphasic" since they show bright signal on T2-weighted, and intermediate to low signal on T1-weighted images.

Enteric contrast may also be dark or "negative" at both T1- and T2-weighted sequences and give signal that is similar to or lower than that of soft tissue at both sequences. Contrast agents such as those containing high concentrations of iron, gadolinium, or manganese may give dark signal at both T1-weighted or T2-weighted sequences. These agents are either expensive or poorly tolerated by patients. Other classes of contrast material that may give dark contrast signal at both T1- and T2-weighted sequences include agents without protons, such as perfluorocarbons. These agents may be delivered in liquid or gaseous form, and may be encapsulated or free in the bowel lumen. Drawbacks of these latter agents include abdominal pain, nausea, potentially dangerous expansion in volume at body temperature compared with room temperature, and anal leakage. High concentration barium or clays may also be used to provide low T1 and low T2 signal.

Another class of material used as dark contrast at both T1- and T2-weighted imaging is free gas, such as room air or carbon dioxide. However, bowel filling with free gas tends to be associated with unfavorable patient discomfort, nausea, and pain. Delivery via an enteric tube may be uncomfortable, and delivery by chemical production of gas in the bowel may be uncomfortable and risk inadvertent bowel perforation by poorly controlled gas expansion. Bowel distension by free gas commonly results in MR imaging artifacts, including susceptibility or dephasing artifact whereby signal loss or image distortions is seen in adjacent tissue on gradient echo sequences, susceptibility-sensitive sequences, and diffusion-weighted sequences. Therefore, there remains in the art a current need for enteric contrast agents with the advantageous contrast properties of gas-based agents that are safely administered, minimize patient discomfort and risk, and provide efficacious and diagnostically useful contrast enhancement in imaging procedures.

BRIEF SUMMARY OF THE INVENTION

The present invention solves the problems noted above by providing MR images acquired after administration to a subject of a safe and effective low T1 and low T2 signal "dark" oral contrast material suitable for human use at MR imaging. The dark T1 and T2 signal is obtained by use of a small particle encapsulating gas or enclosing a partial vacuum. The encapsulated gas or partial vacuum particle contrast agent is delivered in aqueous suspension formulation to distend the bowel lumen and darken the MR signal of the bowel lumen at the time of MR imaging. On T1-weighted and T2-weighted images, the dark signal in the bowel lumen from the contrast agent of the invention is only slightly less dark than that of gas that is naturally present in the bowel lumen, and hence allows for a relatively uniform non-distracting dark appearance of the bowel lumen. Unlike large locules of gas in the native bowel, the very small gas or partial vacuum enclosures within the particles of the invention are too small to cause substantial MR image artifacts on adjacent anatomical structures. The relatively uniform dark appearance of the bowel lumen enabled by use of the contrast medium of our invention allows the reader of the MR images to better visualize the neutral to bright signal structures such as tumors, areas of inflammation, bleeding or other disease which generally appear as neutral to bright signal on T1- and T2-weighted MR images.

An illustration of the nature of the present invention is found in comparing the contrast agents of the current invention with the microbubble contrast agents used in ultrasound imaging. The enteric contrast agents of the present invention are substantially different from microbubble contrast agents used in ultrasound imaging. Microbubbles in ultrasound are usually gas microbubbles of perfluorocarbon gas or nitrogen gas surfaced-coated by flexible material such as albumin, carbohydrates, lipids, or biocompatible polymers that allow ultrasound to cause expansion and contraction of the bubbles, thereby amplifying signal at ultrasound imaging. The mean size of such ultrasound contrast microbubbles is usually in the 2-6 micron range, and the common concentration level is about 10 million microbubbles per mL. Thus, less than 1% of the volume of microbubble-type ultrasound contrast formulations is gas-filled or hollow, and such a small volume fraction of gas or void space does not produce sufficiently low signal to be useful at MR imaging as a dark signal contrast agent. Two recent review articles are given here:

1) Ultrasound microbubble contrast agents: Fundamentals and application to gene and drug delivery By: Ferrara, Katherine; Pollard, Rachel; Borden, Mark. Book Series: ANNUAL REVIEW OF BIOMEDICAL ENGINEERING Volume: 9 Pages: 415-447 Published: 2007;

2) Microbubbles in medical imaging: current applications and future directions. By: Lindner, JR. NATURE REVIEWS DRUG DISCOVERY, Volume: 3 Issue: 6 Pages: 527-532 Published: June 2004

In contrast, the enteric MR contrast materials of the present invention are substantially different from previous perfluorocarbon oral contrast materials proposed for MR imaging. These previous agents include liquid perfluorocarbon, which may or may not be emulsified; these perfluorocarbon also may or may not be brominated. These previous agents are designed such that the perfluorocarbon expand into a gas at body temperature and create dark contrast signal and further bowel distension. Drawbacks of perfluorocarbon agents are that they may be difficult to administer, have an oily texture that may be unacceptable to patients, and their expansile characteristic carries safety concerns when administered into diseased bowel segments.

In various embodiments, the present invention provides the benefits of dark enteric contrast at MR without the interpretation or patient discomfort pitfalls of a free gas. Benefits of dark enteric contrast signal at both T1- and T2-weighted imaging include: superior identification of bowel wall edema and bowel tumors, and superior identification of extra-intestinal soft tissue enhancement compared with existing agents. The liquid medium provides for less discomfort than use of free gas or perfluorocarbon agents since the agent and liquid medium is less likely to expand in volume within the bowel lumen than free gas or perfluorocarbon, and it is not oily in consistency. The encapsulated gas or vacuum suspended in liquid medium also lessens the likelihood of imaging artifacts adjacent to bowel lumen that occur commonly with free gas. The strongly dark signal at T2-weighed images reduces the disorienting changes in signal from markedly bright to markedly dark within adjacent segments of bowel as seen with current non-manganese non-iron containing beverages and dilute barium used for oral contrast material.

Distinct from previous gas-based contrast agents, in an exemplary embodiment the present invention provides a contrast material containing a particle encapsulating a gas or enclosing a vacuum. In exemplary embodiments, the shell is composed primarily of silicon dioxide, silicon-containing rubber, ceramic, polymer, organic material or other biocompatible material and the formulation is composed of encapsulated gas or vacuum particles suspended in a water medium. In various embodiments, the shell is essentially impermeable to water and prevents water or other materials from displacing the encapsulated gas or vacuum. In various embodiments, the shell contains polymers or other substrate to help suspend the particle in an aqueous medium and to improve its palatability.

At MR imaging, exemplary materials of the invention give MR signal that is lower than the range produced by water and non-fat soft tissue. The void that is the gas or partial vacuum contains few or no protons and hence produces minimal or no signal at clinical MR imaging, which obtains signal exclusively or almost exclusively from protons. This absence of signal can be modulated readily by increasing or decreasing the amount of the encapsulated gas or partial vacuum, e.g., by increasing or decreasing the number or size of encapsulated gas or partial vacuum particles, within the aqueous media (i.e., enteric medium)—this is an option not possible with free-gas agents. Also, the containment of the gas or partial vacuum prevents excessive imaging artifact at T2-weighed and T1-weighted MR imaging sequences.

Accordingly, the ability to formulate the particles in a desired enteric medium is accompanied by numerous benefits, including the ability to add excipients that may improve enteric motility and hence the speed of bowel lumen darkening. The use of osmotic excipients in the contrast agent formulation prevents excessive water removal from the contrast agent formulation in the bowel lumen, and thereby allows for more uniform filling of the bowel lumen with the contrast agent. In various embodiments, sugar alcohols, magnesium hydroxide, polyethylene glycol, cellulose, or other materials known to increase bowel transit speed, may be added to the aqueous media.

In various embodiments, excipients may be added to improve the extent of bowel distension. To achieve this goal, excipients such as xanthan gum, guar gum, polyethylene glycol, magnesium hydroxide, cellulose, silica, sugar alcohols, or other fillers may be introduced to alter the thickness of the formulation The agents of the invention may be used alone or in combination with other contrast media. Thus, the dark enteric contrast agent of the invention may be used with an intravenous contrast agent for MR imaging. The dark enteric contrast agent of the invention may be formulated to produce signal that is even lower than that of soft tissue bodily fluid on gradient echo sequences, and thereby improve the conspicuity of intravenous contrast material enhancement of the bowel wall and adjacent vascularized structures.

The dark enteric contrast agent of the invention may be used for functional MRI studies. Thus, the contrast agents of the invention find use in functional studies of the bowel at MRI, including assessment of bowel peristalsis or absence of peristalsis, which may occur in various disease states. Movement of the bowel wall may be quantified on serial non-fat saturation images since the low signal bowel lumen would be markedly different in signal than surrounding intraperitoneal fat or solid organ soft tissues. Bowel transit time may be assessed by timed studies of the transit of the contrast agent under MR imaging monitoring.

In an exemplary embodiment, the invention provides a contrast medium formulation that may also be delivered into the digestive system and other bodily cavities that may be natural such as the vagina or bladder, or surgically created such as neobladders, or artificial medical devices such as tubes, catheters, pouches, reservoirs, or pumps.

In various embodiments, the invention provides a means of acquiring an MRI image of the subject to whom the agent of the invention is administered in which the image is acquired through one or more region of interest (ROI) in the subject's gastrointestinal tract, e.g., esophagus, stomach, duodenum, large intestine, small intestine. In various embodiments, the contrast agent does not appreciably alter contrast of other anatomic structures located in the abdomen or pelvic region of the subject. Thus, for example, an exemplary image of a subject does not include within the ROI organs of the subject's reticuloendothelial system, or urinary system showing contrast attributable to distribution of the enteric agent of the invention in one or more organ of the reticuloendothelial or urinary system of the subject.

In various embodiments, the invention provides an MR image acquired by a method of the invention utilizing a contrast medium of the invention. In various embodiments, the MR images acquired utilizing a contrast medium of the invention show darker signal in the bowel lumen than that of the soft tissue such as the bowel wall, muscle, lymph nodes, or tumors on either or both T1-weighted and T2-weighted images, without substantial image artifact on the bowel wall. In various embodiments, the MR images acquired utilizing a contrast medium of the invention show darkening of the bowel lumen to below that of endometriomas, blood products, intravenous contrast enhanced tissue, or bright signal partially or fully digested food on T1-weighted images, but do not show substantial T1-weighted image artifact (are essentially free of T1-weighted image artifact) on the bowel wall or other anatomic structures adjacent to the darkened bowel lumen. In various embodiments, the MR images acquired utilizing a contrast medium of the invention show darkening of the bowel lumen to below that of water, bowel wall edema, ascites, cysts, or abscesses on T2-weighted images, but do not show substantial image artifact on the bowel wall or other anatomic structures adjacent to the darkened bowel lumen. In various embodiments, the MR images acquired utilizing a contrast medium of the invention do not show paradoxical brightening of the bowel lumen above that of water signal on T1-weighted images when the contrast medium is diluted such as by natural enteric secretions.

In an exemplary embodiment, the image of the invention displays no detectable image artifact involving the bowel wall around the bowel lumen filled with the exemplary enteric contrast agent of the invention.

Other embodiments, objects and advantages of the invention will be apparent from the detailed description that follows.

DETAILED DESCRIPTION OF THE INVENTION

I. Introduction

Figures 1A, 1B, 1C, 1D, 1E:
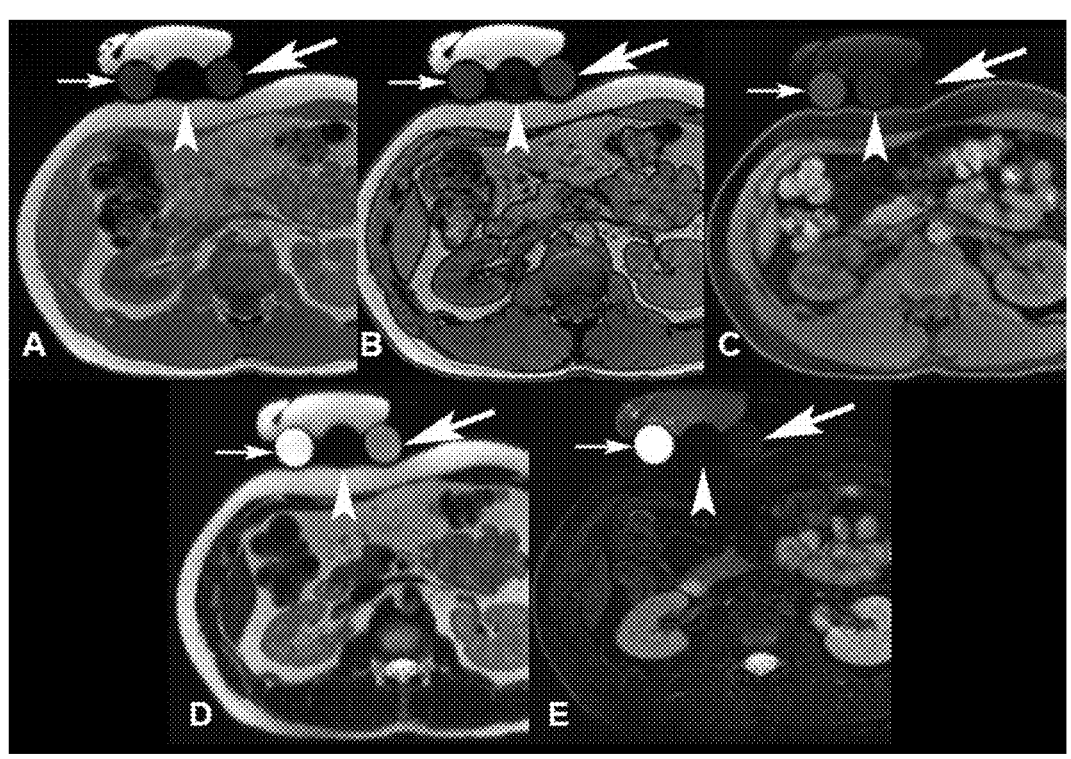
FIG. 1A-FIG. 1E shows signal intensities of vials of exemplary encapsulated gas or partial vacuum contrast material at 3T MRI scan on the abdomen of a volunteer. Three vials of contrast material were placed on the abdomen of a volunteer and scanned on a commercial clinical 3T MR scanner (Skyra, Siemens Healthcare, Germany). The conventional aqueous contrast material VoLumen™ (small arrows) shows intermediate signal on A) T1 weighted in phase, B) T1-weighted opposed phase, and C) T1-weighted fat saturation gradient echo sequences similar to the signal water or soft tissues. The conventional aqueous contrast material also shows intense high signal on D) T2-weighted single shot and E) T2-weighted fast spin echo fat saturation sequences similar to the signal of water. By comparison, an exemplary 20% wt/wt encapsulated gas or partial vacuum contrast material with borosilicate glass shell (true density of particle 0.45 g/cc) in aqueous media (arrowhead) shows signal lower than that of soft tissue on all MR sequences, regardless of whether the sequence is T1- or T2-weighted, and regardless of fat saturation. A third vial (large arrow) contains a 75% silicone oil emulsion which shows intermediate to high signal on the non-fat saturation sequences, and very low signal on the fat saturation sequences, regardless of whether T1 or T2 weighting was used. A bag of canola oil overlies the vials of contrast agents. Commercially available VoLumen contrast material (Bracco, Italy) is composed of water, sorbitol, and 0.01% barium sulfate, The MR sequence parameters were: A & B) Opposed and In phase, respectively: Flip angle 70 degrees, slice thickness 3.5 mm, slice spacing 4.2 mm, Repetition time 170 msec, Time to echo 1.3 msec (for opposed phase) and 2.48 msec (for in phase), matrix 256×208. Window width/level 1490/72. C) T1-w with fat saturation (VIBE): Flip angle 9.0 degrees, Slice thickness 3.0 mm, slice spacing 1.5 mm, Repetition time 3.06 msec, time to echo 1.2 msec, matrix 320×190, Window width/level 584/26. D) T2 without fat saturation (SS HASTE): Flip angle 160 degrees, Repetition time 1600 msec, Time to echo 96 msec, Slice thick 3.0 mm, slice spacing 3.6 mm, matrix 320×194, Window width/level 2071/951. E) T2 with fat saturation (T2 turbo spin echo): Flip angle 160 degrees, slice thickness 5.0 mm, slice spacing 6.0 mm, Repetition time 3000 msec, time to echo 101 msec, matrix 320×240, Window width/level 764-325

A critical shortcoming with images acquired after administration to a subject of current biphasic MR enteric contrast agents is their poor ability to delineate bowel wall edema and high signal bowel tumors at T2-weighted imaging because the high T2 signal of the agents resembles the signal of edema, and of many tumors. A further current problem with acquiring such images is the commercial scarcity in many countries of dark MR contrast agents, the poor taste and appearance of the agents, and unpleasant side effects. The present invention provides images with excellent dark (low) signal at both T1 and T2-weighted MR sequences to allow delineation of bowel wall edema and tumors at T2-weighted imaging, and visualization of intravenous contrast enhancement of bowel wall and tumors on T1-weighted images. The invention provides an enteric contrast medium formulation that is palatable and gives minimal discomfort following administration to a subject.

At MR imaging, the signal of the present contrast material resembles that of naturally occurring gas within the bowel lumen at both T1- and T2-weighted imaging. This beneficial characteristic provides a uniform low signal appearance of the bowel lumen which thereby allows bright signal disease states to be emphasized. Uniform low signal improves upon that of current biphasic MR contrast agents which produce bright high signal at T2-weighted imaging that may give a visually confusing appearance of bowel lumen that frequently also contains low signal bowel gas. In an exemplary embodiment, images of the invention including the enteric contrast medium of the invention within a region of interest display the agent as having an intensity essentially indistinguishable from naturally occurring gas in the bowel. In various embodiments, a radiologist experienced in reading MR images would detect at most a 50% difference between the enteric contrast medium and naturally occurring gas, preferably at most 25% and preferably at most 10% on visual interpretation of the images of the invention Prior dark enteric MR contrast agents based on fluorocarbons show marked volume expansion of the agent at body temperature compared to room temperature, and thereby caused abdominal discomfort and risked bowel perforation. Also, the oily nature of these agents resulted in poor patient tolerance and anal leakage. The enteric medium of the invention includes non-expansile gas and partial vacuum particles, thereby reducing the discomfort and risk to patients since the formulations of the invention behave as simple aqueous suspensions and do not change appreciably in volume from room to body temperature, i.e., following administration to a subject.

Our invention, in various embodiments, provides MR images through a ROI of a subject through which is distributed a contrast agent with one or both of the following properties: 1) Substantially lower MR signal than both fat and intravenous gadolinium contrast material on T1-weighted images; and 2) substantially lower MR signal than both fluid and fat on T2-weighted images. Our invention, in various embodiments, also provides for a palatable agent that passes rapidly through the intestinal tract and provides good distension of the bowel lumen for improved MR imaging. Also provided are contrast agents having these properties, formulations including such contrast agents and methods of acquiring MR images of a subject to whom the agent or formulation has been administered.

II. Definitions

Unless defined otherwise, all technical and scientific terms used herein generally have the same meaning as commonly understood by one of ordinary skill in the art to which this invention belongs. Generally, the nomenclature used herein and the laboratory procedures in organic chemistry, pharmaceutical formulation, and medical imaging are those well known and commonly employed in the art.

The articles "a" and "an" are used herein to refer to one or to more than one (i.e. to at least one) of the grammatical object of the article. By way of example, "an element" means one element or more than one element. Contrast agents with iodine, barium or other atoms with Z greater than 40 are exemplary "high Z" materials.

A "disease" is a state of health of an animal wherein the animal cannot maintain homeostasis, and wherein if the disease is not ameliorated then the animal's health continues to deteriorate.

"Contemporaneous" administration refers to use of a contrast agent in conjunction with a medical imaging procedure (e.g., MR) performed on a subject. As understood by one of skill in the art, contemporaneous administration of the contrast agent to the subject includes administration during or prior to the performance of the medical imaging procedure such that the contrast agent is visible in the medical image of the subject.

The term "half-life" or "t½", as used herein in the context of administering an enteric contrast medium of the invention to a patient, is defined as the time required for enteric concentration of a drug in a patient to be reduced by one half. There may be more than one half-life associated with the contrast medium depending on multiple clearance mechanisms, redistribution, and other mechanisms well known in the art. Further explanation of "half-life" is found in Pharmaceutical Biotechnology (1997, DFA Crommelin and RD Sindelar, eds., Harwood Publishers, Amsterdam, pp 101-120).

"Enteric contrast medium formulation" as herein used means, unless otherwise stated, a pharmaceutically acceptable liquid or paste formulation for administration to a subject, which comprises at least one enteric contrast medium, and with or without at least one pharmaceutically acceptable excipient as the suspending agent, and which is prepared by dissolving, emulsifying, or suspending an enteric contrast medium as herein described, e.g. in the form of a powder, emulsion or mash, in a pharmaceutically acceptable vehicle, before use for administration to the subject. Preferably the pharmaceutically acceptable vehicle is water-based. An exemplary enteric contrast medium formulation is of use in the acquisition of a contrast enhanced MR image of the gastrointestinal tract of a subject undergoing such imaging. An exemplary enteric contrast medium formulation is administered to a subject via an oral route and the formulation is well-tolerated by the patient as its taste, odor and appearance is inoffensive.

The term "residence time", as used herein in the context of administering an enteric contrast medium to a patient, is defined as the average time that the enteric contrast medium stays in the body of the patient after dosing. More particularly, this term refers to a period of residence of an agent in the gastrointestinal tract of a subject undergoing a contrast enhanced MR imaging study with an agent of the invention. Further, more particularly, during this period of residence an exemplary agent remains largely functionally intact such that the agent produces the desired signal within the ROI at the time of MR imaging. By way of example, a desirable residence time is at least as long as the time needed to acquire an MR image of at least a portion of the subject's gastrointestinal tract (i.e., ROI) such that the image displays contrast-related darkened signal within the bowel lumen that is lower in intensity (darker) by at least about 10%, at least about 30%, or at least about 50% of the intensity within a substantially identical image of substantially the same ROI absent the contrast agent of the invention. By way of example, an undesirable residence time is at least as long as the time needed to acquire an MR image of the bowel, but is sufficiently long that during that time the contrast agent is damaged or disrupted such that the MR image does not display substantial contrast-related darkened signal within the bowel lumen.

The term "magnetic resonance" (MR) refers to magnetic resonance imaging of any sort, including low field, 1.5 Tesla, 3 Tesla, and high field (4 Tesla and above).

The term "enteric contrast medium" as used herein is understood to mean a dry or unsuspended component or mixture of components comprising at least one substance that contributes to lower the MR signal on T1 and T2 weighted images in an ROI containing the contrast medium and, optionally, at least one pharmaceutically acceptable carrier, which may itself include other components, e.g., taste-masking agents, antioxidants, wetting agents, emulsifying agents, etc. The enteric contrast medium is preferably suspended in a suspending medium to form the enteric contrast medium formulation of the invention. In a particular embodiment, the term enteric contrast medium refers to a contrast medium that distributes substantially in a subject's gastrointestinal tract as opposed to other organ systems. In one embodiment, the enteric contrast medium of the invention is essentially excluded from distribution into the reticuloendothelial system (RES) or, put another way, to the extent the agent of the invention distributes into the RES, it is not useful as an MR contrast agent in this organ system when so distributed. Accordingly, images of the invention in which an ROI includes at least a portion of a subject's RES do not show useful levels of contrast in the RES anatomy displayed in the ROI attributable to the enteric contrast medium.

As used herein, "pharmaceutically acceptable carrier" includes any material, which when combined with the gas/vacuum particles, these particles are retained usefully in suspension and the resulting formulation is non-reactive with the subject's immune and other systems. Examples include, but are not limited to, any of the standard pharmaceutical carriers such as a phosphate buffered saline solution, water, emulsions such as oil/water emulsion, and various types of wetting agents. Other carriers may also include sterile solutions. Typically such carriers contain excipients such as starch, milk, sugar, sorbitol, methylcellulose, certain types of clay, gelatin, stearic acid or salts thereof, magnesium or calcium stearate, talc, vegetable fats or oils, gums, glycols, or other known excipients. Such carriers may also include flavor, texture, and color additives or other ingredients. Compositions comprising such carriers are formulated by well-known conventional methods. Exemplary carriers provide a suspension of the enteric contrast particles which is stable (particles do not appreciably settle or agglomerate) on storage for at least about 30 minutes, at least about 60 minutes, at least about 120 minutes. Certain formulations of the invention are characterized by long term stability and are stable for at least about 12 hours, at least about 24 hours or longer. Exemplary formulations of the invention display these levels of stability at 25° C. An exemplary carrier is one that does not interfere with, compete with or counteract the darkening properties of the agent of the invention in the images of the invention.

As used herein, "administering" means oral administration, administration as a suppository, topical contact, intrarectal, intravenous, intraperitoneal, intramuscular, intralesional, intranasal or subcutaneous administration, intrathecal administration, or instillation into a surgically created pouch or surgically placed catheter or device, or the implantation of a slow-release device e.g., a mini-osmotic pump, to the subject. A preferred route of administration is oral administration.

The terms "coating" and "coated" as herein used are understood to include coatings which are biocompatible within an environment having an acidic, or a neutral, or a basic pH value.

The terms "particle" and "particles" as used herein refers to free flowing substances of any shape which are larger than about 20 nm, such as crystals, beads (smooth, round or spherical particles), pellets, spheres, and granules. A particle may be a hollow sphere with a central void or contain multiple internal cavities forming a void network. Exemplary specific sizes for the particles include from about 20 nm to about 500 microns, e.g., 1 micron to about 100 microns, encompassing each single diameter value and each diameter range within the larger range across all endpoints; in various embodiments, the particles are larger than about 5 microns. Further useful particle sizes include, for example, from about 5 microns to about 100 microns, e.g., from about 20 microns to about 70 microns. A preferred particle contains gas or partial vacuum. The gas or partial vacuum in preferred particles allows the particles to be displayed in an image of the invention as a region, which is darkened relative to the soft tissue adjacent the particles provided to the subject by administering a formulation of the invention.

The term "suspending agent" as used herein refers to any convenient agent known in the art to be of use in forming and/or maintaining a suspension of a particulate solid in a liquid (e.g., aqueous or oil). Exemplary suspending agents are selected from xanthan gum, guar gum, hydroxypropylmethyl cellulose, hydroxypropyl cellulose, polyvinyl pyrrolidone, alginates, and sodium carboxylmethylcellulose. Xanthan gum is a preferred suspending agent. Suspending agents may be employed in any useful amount. Exemplary useful amounts of a suspending agent are within the range from about 0 to about 20% by weight of the powder enteric contrast medium formulation, and from about 0 to about 10% by weight of the liquid oral suspension enteric contrast medium formulation. In various embodiments, the suspending agent is dissolved in the carrier. In various embodiments, the suspending agent is within the range from about 0.2 to 0.6% by weight of the enteric contrast medium formulation in aqueous suspension. The invention provides both the powder enteric contrast medium and formulation in which this medium suspended in the carrier/suspending agent mixture.

"Stable" and "stable formulation" in the context of the invention refers to suspensions that do not significantly separate into their components as different phases or layers between formulation of the enteric contrast medium suspension and the administration of the suspension to a subject prior to or during an imaging study. In preferred embodiments, the formulations of the invention are stable formulations.

The term "encapsulated gas or partial vacuum" as used herein refers to gas or vacuum that is confined and highly restricted from communication with the external environment such that a minimal amount of the gas or vacuum is released from the confined space during the expected residence time of biological use. The encapsulated gas may be at a lower, same, or higher pressure than the surrounding atmosphere or suspending liquid vehicle. The confined space is defined by a solid shell, such as a shell formed of a Si-based material as set forth herein.

The term "dark contrast", "dark" and "darker" as used herein refers to material that produces lower MR signal than fat on a non-fat saturated MR image (either T1- or T2), and to the appearance of the contrast agent on a MR image of the invention relative to the tissue adjacent the agent.

"An unpleasant taste" as used herein means that a majority of human patients judges said enteric contrast medium comprised as having an unpleasant taste after ingestion.

III. Exemplary Embodiments

A. Compositions

In various embodiments, the present invention provides enteric or non-vascular, non-RES, contrast agents that produces low signal at T1- and intermediate to low signal on T2-weighted MR images (dark, darker). By use of encapsulated gas or partial vacuum particles, with or without high susceptibility materials such as iron, contrast agents can be created that have a markedly low MR signal that is lower than fat and soft tissue signal. As an example, gas or vacuum can be encapsulated by any biocompatible material, including organic and inorganic polymers, and glasses. Exemplary materials include silicon-based material (e.g., $SiO_2$, e.g., glass), ceramic, plastic, or other solid shell material. In various embodiments, the encapsulating material is of use to modulate the MR signal of the overall particle and thereby create new contrast material formulations with useful low MR signal properties. The agents of the present invention provide a new class of contrast materials with adjustable MR signal in the low signal range. An exemplary useful application of the agents of the invention is the acquisition of MR images in which the bowel lumen is distinguished from body tissues e.g., soft tissue) and pathological states of the bowel wall.

In various embodiments, the shell of the particles of the contrast medium of the invention are formed from inorganic materials, e.g., silica, alumina, ceramics, borosilicate glass. Exemplary particle shells include more inorganic atoms than organic atoms by weight. Exemplary particle shells are formed from an organic polymer. Exemplary organic polymer shell particles are formed from polymers or copolymers prepared from acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ¿-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-aminostyrene, p-amino-benzylstyrene, sodium styrene sulfonate, sodium 2-sulfoxyethylmethacrylate, vinyl pyridine, aminoethyl methacrylates, 2-methacryloyloxy-trimethylammonium chloride, and polyvinylidene. In various embodiments, the shell of the particles of the invention are formed from polyfunctional crosslinking monomers such as N,N'-methylenebisacrylamide, ethylene glycol dimethacrylates, 2,2'-(p-phenylenedioxy) diethyl dimethacrylate, divinylbenzene, triallylamine and methylenebis-(4-phenyl-isocyanate), or combinations thereof. Exemplary shells of the particles of the invention include polyacrylic acid, polyethyleneimine, polymethacrylic acid, polymethylmethacrylate, polysiloxane, polydimethylsiloxane, polylactic acid, polys-caprolactone), epoxy resin, poly(ethylene oxide), poly(ethylene glycol), and polyamide (nylon). Further exemplary particle shells of the particles of the invention include copolymers including the following: polyvinylidene-polyacrylonitrile, polyvinylidene-polyacrylonitrile-polymethylmethacrylate, and polystyrene-polyacrylonitrile. In an exemplary embodiment, the shells of the particles of the contrast medium of the invention is formed of a material other than the copolymer polyvinylidene-polyacrylonitrile.

In various embodiments, the true density of the particles is greater than about 0.05 g/cm³. In various embodiments, the true density of the particles of the contrast medium of the invention is at least about 0.1, at least about 0.3, at least about 0.5, at least about 0.7, at least about 1, at least about 1.5 or at least about 2 g/cm³.

Exemplary particles of the invention are at least partially evacuated. In various embodiments, the interior space of the particle defined by the shell has a pressure of less than or equal to about 1 atmosphere, e.g., less than about 0.8 atm, less than about 0.6, atm, less than about 0.3 atm or less than about 0.1 atm.

In various embodiments, the interior space of the particle is at least partially gas filled as discussed herein. In various embodiments, the gas within the particle is the ambient air present when the particle was formed, it can also be a gaseous mixture with which the particle precursor material(s) was contacted during manufacture of the particles. When the interior of the particle is at least partially filled with a gas other than air, the gas is preferably not a hydrocarbon, fluorocarbon or a hydrofluorocarbon. In various embodiments, the gas is an elemental gas. In various embodiments, the gas is sulfur-based or oxygen-containing.

In various embodiments, the gas is other than xenon, argon, neon, helium, air or a combination thereof. In an exemplary embodiment, the gas is a molecule including at least one sulfur atom. In various embodiments, the gas is carbon dioxide, oxygen, nitrogen, sulfur dioxide, or a combination thereof. In an exemplary embodiment, the particle encapsulates at least a partial pressure of a gas containing oxygen, carbon dioxide and nitrogen.

In operation, the particles of the contrast medium of the invention have distinctive properties compared to other particulate contrast media. For example, particles of an exemplary contrast medium of the invention do not increase the MR signal on T1- or T2-weighted MR images of the contents of the lumen of the gastrointestinal tract or other body cavities. In various examples, the particles of the contrast medium decrease the MR signal on T1- or T2-weighted MR images of the contents of the lumen, of the intestinal tract or other body cavity.

In various embodiments, the invention provides a MR image of a ROI of a subject including bowel lumen of the subject. In the exemplary MR images, the contents within the lumen in which the contrast medium is distributed display decrease in MR signal on T1- or T2-weighted images including the ROI. In the exemplary MR images, the contents within the lumen in which the contrast medium is distributed do not display an increase in MR signal on T1- or T2-weighted images including the ROI. Exemplary MR images acquired through a gastrointestinal tract structure including a contrast medium of the invention are provided in the Figures appended hereto.

Exemplary contrast media of the invention decrease the MR signal (darken) of the lumen of the gastrointestinal tract or other body cavity to below that of fat on a non-fat saturated T1- or T2-weighted images. Exemplary particles of the contrast medium decrease the MR signal (darken) of the lumen of the gastrointestinal tract or other body cavity to below that of soft tissue on a T1- or T2-weighted image. Accordingly, exemplary MR images of the invention include an ROI incorporating lumen of the gastrointestinal tract or other body cavity for which the signal is reduced to below that of fat on a non-fat saturated T1- or T2-weighted images. In various embodiments, exemplary MR images of the invention include an ROI incorporating lumen of the gastrointestinal tract or other body cavity for which the signal is reduced to below that of soft tissue on a T1- or T2-weighted image.

In various embodiments, the invention provides an MR image with an ROI incorporating bowel lumen of a subject in which the contrast medium of the invention is distributed. The image shows darkening of the bowel lumen on T1-weighted and T2-weighted imaging without noticeable image artifact Exemplary contrast agents of our invention provide improved MR imaging applications with one or more of the following benefits:

1) The lumen of bowel or other hollow non-vascular structures that contain the contrast material of the invention are more easily differentiated from soft tissue than if filled by currently available biphasic MR contrast material;

2) The lumen of bowel or other hollow non-vascular structures can be distended by contrast materials of the invention and be distinguished at MR imaging from vascular structures or soft tissue enhanced by intravenous MR contrast agents that increase the T1-signal (T1-shortening MR contrast agents);

3) The MR image signal in the lumen of enteric or other hollow nonvascular structures can be darkened with contrast of the invention without interfering with the assessment of intravascular contrast material related mural enhancement of those structures (bowel wall, bladder wall, other walls, including associated disease such as inflammation or neoplasms); and 4) Are essentially excluded from the vasculature of the subject to whom they are administered.

In various embodiments, the invention provides enteric contrast agents based on particles encapsulating gas or a partial vacuum. In various embodiments, the contrast agent is selected to provide a very low MR signal, such as, signal that is lower than that of fat, soft tissue, or water. In various embodiments, the contrast agent formulation includes gas or partial vacuum encapsulated in particles in an aqueous media.

Exemplary encapsulating materials of the encapsulated gas or partial vacuum particle of the invention may be a glass, gel, resin, ceramic, metal, polymer, or rubber, or a combination of more than one of these materials.

In an exemplary embodiment, the encapsulating material for the gas or partial vacuum of the particle is a glass. Exemplary glasses of use in the particles of the invention are those containing silicon dioxide, e.g., silicon dioxide blended with additives such as potash (potassium oxide), soda (sodium carbonate or sodium oxide), sodium oxide, lime (calcium oxide), boron trioxide, boric acid, magnesia, alumina, iron oxide, or other oxides. In an exemplary embodiment, the glass shell of the hollow microspheres contains silicon oxide as the sole or main component, and other chemical ingredients (mainly oxides) in the glass mentioned above are in minor quantities for the purpose of improved melting, processing and property modifications, as found in the current art of glass industry. In an exemplary embodiment, a shell of borosilicate glass consists of about 80% silica, about 13% boric oxide, about 4% sodium oxide and about 2-3% aluminum oxide.

In various embodiments, the particle is formed of a shell material defining an internal void. Exemplary shell materials contribute no or minimal protons to the formulation. In various embodiments, the shell material contains essentially no ferromagnetic or diamagnetic materials which may contribute to the low T1 or low T2 signal of the formulation. In various embodiments, the shell material contains ferromagnetic or diamagnetic materials which may contribute to the low T1 or low T2 signal of the formulation.

In an exemplary embodiment, the encapsulated gas within the particle includes one or more of a sulfur-containing gas, oxygen, carbon dioxide, nitrogen or a combination thereof. In various embodiments, the gas is sulfur dioxide or sulfite. In various embodiments, the gas is a combination of oxygen, nitrogen and carbon dioxide.

In an exemplary embodiment, the encapsulated gas or partial vacuum particle has a true density of from about 0.1 to about 1.6 g/cc. In an exemplary embodiment, the encapsulated gas or partial vacuum particle has a true density of between 0.1 and 1.0 g/cc. In an exemplary embodiment, the encapsulated gas or partial vacuum particle has a true density of from about 0.15 to about 0.6 g/cc. In a preferred embodiment, the true density is from about 0.2 to about 0.6, including about 0.2, about 0.3, about 0.4, about 0.5, and about 0.6. As used in this context, "about" means+/−0.05.

Exemplary encapsulated gas or partial vacuum particles of use in the formulations of the invention include borosilicate microspheres having a true density similar to that of water (e.g., from about 0.15 to about 1.5 g/cc). Preferred true densities are from about 0.2 to about 0.6 g/cc. As used in this context, "about" means+/−0.05.

One or two or more encapsulated gas or partial vacuum particle may be used together in which the particles differ in the identity of the gas, pressure of the gas, internal pressure of the partially evacuated particle and a combination thereof.

Any useful suspending agent or combination of suspending agents can be utilized in the formulations of the invention. In various embodiments, the suspending agent is thixotropic and forms a gel-like medium at rest but a liquid with agitation.

In an exemplary embodiment, the encapsulated gas or partial vacuum particle is suspended in a pharmaceutically acceptable carrier to form an enteric contrast medium.

In various embodiments, ferromagnetic materials such as iron or manganese is present in the shell of the particle, or in the contrast formulation as separate suspended particles or as dissolved material in the aqueous or oil-based vehicle to provide lower T1 or T2 signal of the overall contrast medium formulation. In an exemplary embodiment, the particles are suspended in a combination of the carrier and a suspending agent.

In an exemplary embodiment, the encapsulated gas or partial vacuum particle is coated to provide useful properties for the contrast material, such as improved suspension in media, increased true density, or altered T1 or T2 MR signal when scanned at MR imaging.

In an exemplary embodiment, the coating comprises an organic molecule with a molecular weight of less than about 3 kd, less than about 2 kd or less than about 1.5 kd. In an exemplary embodiment, the coating comprises an organic molecule with a molecular weight of less than about 3 kd, less than about 2 kd or less than about 1.5 kd, which is a member selected from an organic acid (or alcohol, amine) and its derivatives or analogs, an oligosaccharide and a combination thereof.

In an exemplary embodiment, the coating is a protein, e.g., albumin.

In various embodiments, the particles of the invention are coated with a biocompatible coating. Appropriate coatings are known in the art and it is within the abilities of one of skill in the art to select an appropriate coating for a particular formulation and/or application. See, for example, Yeh BM, Fu Y, Desai T, WO 2014145509 A1).

In various embodiments, the particles of the contrast agent are essentially stable across administration and the residence time in the subject. As used herein "essentially stable" refers to a population of particles in which a substantial fraction of the encapsulated gas or partial vacuum particles do not break, leak or take on, or fill with, liquid until after the MR imaging is complete. In various embodiments, the invention provides a contrast medium formulation of essentially stable particles in which less than about 10% of the encapsulated gas or partial vacuum particles in liquid suspension break, leak or take on, or fill with, liquid when remaining in suspension for extended periods of time. Exemplary extended period of time include 6 month, 12, months, 18 months, 24 months and longer. An exemplary formulation of the invention includes particles in which less than about 10% of the encapsulated gas or partial vacuum particles in liquid suspension break, leak or take on, or fill with, liquid following administration to a subject and during their residence time within the subject.

A "solid shell" refers to a shell sufficiently impermeable to retain the gas or maintain the partial vacuum present on manufacture of the particle, as well as retard or prevent the passage of liquid into the void formed by the solid shell, following administration of the agent of the invention to a subject and for at least the duration of the imaging experiment. A solid shell is distinguished in definition and physical and chemical form from reversible particles, e.g., a micelle, a liposome or an emulsion, e.g., a perfluorocarbon or other emulsion, in which air (or other gas) bubbles may be entrapped, entrained or stabilized.

The suspended phase of formulations of the invention can include particles of any useful size. Exemplary specific diameters for the particles include from about 1 nm to about 500 microns, e.g., 1 micron to about 100 microns. In various embodiments, the particles are larger than about 5 microns. Further useful particle sizes include, for example, from about 5 microns to about 100 microns, e.g., from about 20 microns to about 70 microns. In various embodiments, the particle is a solid shell encompassing a void in which a gas or a partial vacuum is maintained. In various embodiments, the diameter of the void space within the particle corresponds to the diameters set forth above. The specified ranges encompass each single diameter value and each diameter range within the larger range across all endpoints.

The formulations of the invention can include the particulate contrast agent in any useful concentration. In various embodiments, from about 5% (w/w, expressed as a weight percent, e.g. about 5 grams of contrast medium particle contained in about 100 grams of total contrast medium formulation) to 50% (w/w) of the weight of said formulation is said particles. In an exemplary embodiment, the particles make up about 5% (w/w) to about 25% (w/w) of the liquid suspension contrast medium formulation. In various embodiments, the formulation includes from about 5% (w/w) to about 20% (w/w) of the particles. In an exemplary embodiment, the invention provides a liquid suspension contrast medium formulation comprising from about 5% (w/w) to about 12% (w/w) of the particles. An exemplary formulation includes about 9% (w/w) of the particles. As used in this context, "about" means+/−0.05%.

The formulations of the invention can include a single enteric contrast medium or two or more enteric contrast media. The individual particulate media can be present in similar or different concentrations according to any useful measure of concentration. An exemplary embodiment includes different concentrations of one or more particles or soluble agents that each contribute substantially to the MR signal, relative to that of water, in the overall contrast formulation. The preceding disclosure of exemplary useful concentrations of particles is applicable here and can refer to each individual particle population or the entire population of different particles in the aggregate.

The liquid suspension formulations of the invention include a population of encapsulated gas or partial vacuum particles of the invention suspended in a pharmaceutically acceptable carrier vehicle. The vehicle includes any other useful component. For example, in some embodiments, the vehicle comprises an aqueous medium, and it further comprises an additive to impart a second property to the formulation, for example, retard dehydration of said formulation in the bowel, provide flavoring, stabilize the suspension, enhance flowability of the suspension, thicken the suspension, provide pH buffering and a combination thereof.

Within the scope of the invention are formulations designed for single dosage administration. These unit dosage formats contain a sufficient amount of the formulation of the invention to provide detectable contrast in a subject to whom they are administered. In an exemplary embodiment, the unit dosage formulation includes a container holding sufficient enteric contrast medium to enhance, in a diagnostically meaningful manner, a diagnostic image of a subject to whom the unit dosage has been administered. The container can be a vial, an infusion bag or any other appropriate vessel. The enteric contrast medium may be in the form of a preformulated liquid, a concentrate, or powder. In an exemplary embodiment, the subject weighs about 70 kg. In an exemplary embodiment the image is measured through the abdomen of the subject, the pelvis of the subject, or a combination thereof.

In various embodiments, the unit dosage formulation includes from about 800 to about 1500 mL of the contrast medium per adult human dose, which may be divided into smaller containers such as from about 300 to about 600 mL in size. In an exemplary embodiment, the enteric contrast medium formulation is a unit dosage formulation of from about 50 to about 100 mL. In an exemplary embodiment, the enteric contrast medium formulation is a unit dosage formulation of from about 100 mL to about 800 mL.

Any of the formulations described herein can be formulated and utilized for administration through any of a variety of routes. Exemplary routes of administration include oral, rectal, intravaginal, intravascular, intrathecal, intravesicular, and the like.

In various embodiments, the enteric contrast medium of the invention exhibits chemical stability across a wide pH range (e.g., from about 1.5 to about 10). The stomach exposes enteric contents to low pH of 1.5 and bile and small bowel may expose enteric contents to high pH of up to 10. Excessive degradation of the enteric contrast medium may result in loss of the low signal of the enteric contrast medium formulation on T1- and T2-weighted MR images. Also, physicochemical stability is a critical component of safety and helps minimize the risk of reactions or adverse events. Adverse reactions may occur if excessive dissolution or degradation of the enteric contrast medium were to occur in the gastrointestinal tract, or if the breakdown products are potentially toxic.

In various embodiments, the encapsulated gas or partial vacuum particle has a pH that would not cause injury to the patient. In an exemplary embodiment, the encapsulated gas or partial vacuum particle has a neutral pH (5.5 to 9) in aqueous suspension. In an exemplary embodiment, the encapsulated gas or partial vacuum particle has a mildly to moderately alkaline pH (8 to 10.5) in aqueous suspension.

In various embodiments, the invention provides an enteric contrast medium and a formulation of a contrast medium with a t½ that is sufficiently long to allow the completion of an imaging experiment with the concentration of encapsulated gas or partial vacuum particle remaining sufficiently high within the region of interest. In various embodiments, the invention provides an enteric contrast medium and a formulation having an in vivo residence time that is sufficiently short to allow essentially all of the administered encapsulated gas or partial vacuum particles to be eliminated from the body of the subject before being altered (metabolized, hydrolyzed, oxidized, etc.) by the subject's body.

In various embodiments, the small bowel enteric transit time of the formulation is less than 12 hours in normal subjects. In an exemplary embodiment, the formulation includes sorbitol, polyethylene glycol or both to accelerate enteric transit times.

In an exemplary embodiment, the invention provides an enteric contrast medium that dissolves or degrades slowly such that the majority of the administered encapsulated gas or partial vacuum particles are eliminated via the gastrointestinal tract prior to being altered by the subject's body, and a dissolved or altered portion is excreted by the urinary tract.

The pharmaceutical formulation of the present invention may optionally include excipients and other ingredients such as one or more sweeteners, flavors and/or additional taste modifiers to mask a bitter or unpleasant taste, suspending agents, glidants, antioxidants, preservatives and other conventional excipients as needed.

The suspension of the invention may optionally include one or more antioxidants, if necessary, taste modifiers, sweeteners, glidants, suspending agents, and preservatives.

As will be appreciated, the above optional ingredients may be added to the powder formulation of the invention, or to the oral suspension of the invention.

Antioxidants suitable for use herein include any convenient agents known in the art for this purpose such as sodium metabisulfite, sodium bisulfite, cysteine hydrochloride, citric acid, succinic acid, ascorbic acid, sodium ascorbate, fumaric acid, tartaric acid, maleic acid, malic acid, EDTA with sodium metabisulfite or sodium bisulfite being preferred.

Antioxidants may be employed in an amount which will protect the formulation from oxidation as will be apparent to one skilled in the art.

Sweeteners for use in the formulations of the invention may be any convenient agents known in the art for this purpose and may be selected from any compatible sweetener groups such as natural sweeteners like sucrose, fructose, dextrose, xylitol, sorbitol, or manitol, as well as artificial sweeteners such as aspartame, acesulfame K and sucrolose. Xylitol and aspartame are preferred sweeteners.

Flavors and flavor modifiers or taste modifiers can also be used to further improve the taste and can be any convenient agents known in the art for this purpose and include, but are not limited to, orange flavor, vanilla flavor, licorice flavor, orange vanilla flavor, creme de mint, cherry flavor, cherry vanilla flavor, berry mix flavor, passion fruit flavor, pear flavor, strawberry flavor, mandarin orange flavor, bubble gum flavor, tropical punch flavor, juicy compound for grape, grape flavor, artificial grape flavor, grape bubble gum flavor, tutti-frutti-flavor, citrus flavor, lemon flavor, chocolate flavor, coffee flavor, and combinations thereof.

Suspending agents can be any convenient agents known in the art for this purpose and can be selected from xanthan gum, guar gum, hydroxypropylmethyl cellulose, hydroxypropyl cellulose, polyvinyl pyrrolidone, alginates, and sodium carboxylmethylcellulose with xantham gum being preferred. Suspending agents may be employed in an amount within the range from about 0 to about 20% by weight of the powder formulation, and from about 0 to about 10% by weight of the liquid oral suspension formulation.

Preservatives can be any convenient agents known in the art for this purpose and can be selected from the group consisting of any compound compatible with drug actives such as methylparaben and propylparaben, benzoic acid, sodium benzoate, potassium sorbate, with methylparaben being preferred.

The invention also provides kits for use in a clinical and/or research setting. An exemplary kit includes: (a) a first vial containing the enteric contrast medium of the invention; (b) a second vial containing a suspension agent; and (c) directions for using and/or formulating the enteric contrast medium as a suspension. In various embodiments, the kit further comprises another vial containing a second contrast medium; and directions for administering and/or formulating the first and second enteric contrast medium in a clinical or research setting.

B. Methods

The invention also provides methods of utilizing the formulations of the invention to acquire and enhance clinically meaningful MR images from a subject to whom the formulation of the invention is administered. The method includes, administering to the subject a diagnostically effective amount of said enteric contrast medium formulation of the invention; and acquiring the MR images of the subject. Oral administration of the agent is generally preferred. In an exemplary embodiment, the method includes acquiring an image through a structure of the subject's gastrointestinal tract. In various embodiments, the structure includes a lumen defining an interior void and the contrast medium of the invention is distributed within the void, at least within an ROI through which the image is acquired.

The method of the invention utilizes art-recognized clinical and research magnetic resonance imaging devices, data acquisition methods, data processing methods and image creation and analysis methods. Those of ordinary skill in the art are familiar with these procedures and they do not require description herein.

In an exemplary embodiment, the invention provides a contrast enhanced MR image of a subject through a region of the subject in which the enteric contrast medium of the invention is distributed.

The image of the invention, and those acquired by the method of the invention utilize a contrast medium of the invention. The image is taken through any section of the body of the subject. In an exemplary method, the image is through the abdomen and/or pelvis of the subject. In various embodiments, as set forth herein, the image is acquired through a ROI incorporating at least one portion of a subject's gastrointestinal system.

The following Examples are offered to illustrate exemplary embodiments of the invention and do not define or limit its scope.

EXAMPLES

Example 1

Encapsulated gas or partial vacuum microparticles are common, commercially available, and can be produced in many ways well known to practitioners of the art. A common range of methods utilize a "blowing agent," which is a substance that can release gas when heated to a high temperature. An example of production of encapsulated gas or partial vacuum microparticles is to heat shell material (in the form of glass or ceramic frit, powder, or solution) and blowing agent to a temperature sufficient to melt the shell material then cause gas release from the blowing agent to create hollow microparticles that are then cooled. Heating temperatures may range, for example, from 800 to 1500 degrees Celsius as needed for varying shell materials, to make different types of encapsulated gas or partial vacuum microparticles. Another process is to heat porous glass or ceramic material to slightly melt and seal the surface such that a gas or partial vacuum is retained inside the particles. Partial vacuum in the heating chamber can be utilized with the above methods to adjust the resultant fraction and physical characteristics of the resultant encapsulated gas or partial vacuum microparticles in the product. Gravity with or without updraft or downdraft can be utilized to modulate the residence time of particles in the heating zone, thereby influencing the diameter and true density of the resultant encapsulated gas or partial vacuum microparticles. Further selection of microparticle subpopulations can be obtained by a number of mechanical means based on physical characteristics such as diameter or true density.

Due to the safety considerations of enteric MR contrast medium formulations, the microparticle shell materials (silica, glass, borosilicate glass, ceramic, polymer, etc.) are chosen to be biologically safe and inert, e.g. those materials without toxic levels of elements such as lead, cadmium and the like.

Example 2

Stable suspension of encapsulated gas or partial vacuum microparticles in aqueous solution may be obtained by use of a suspension agent. For example, use of 0.15 to 0.5% xanthan gum was used to suspend 10 to 50% wt/wt encapsulated gas or partial vacuum particles (Potters Beads) with true density of 0.34 to 1.2 in water. The resulting suspension of particles remained homogeneous at MR imaging for over 12 months. The viscosity of the suspensions ranged from 50 to 2400 g/cm-sec.

Figure 2A:
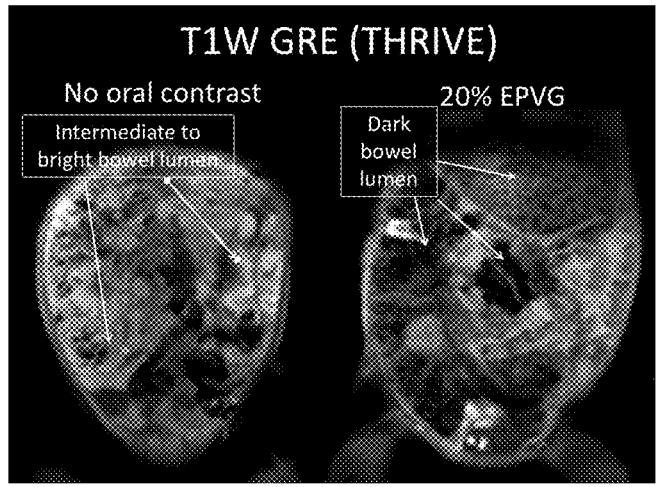
FIG. 2A-FIG. 2B shows exemplary imaging of encapsulated partial vacuum or gas particle enteric contrast material (hollow borosilicate glass microspheres having true density 0.45 g/cc, at 20% wt/wt in aqueous suspension with 0.3% wt/wt xanthan gum) in a rabbit on a 1.5T MR scanner. A) Coronal T1-weighted gradient echo fat saturation images of a 3 kg rabbit without (left image) and with (right image) enteric administration of 20% wt/wt encapsulated partial vacuum or gas hollow borosilicate glass particles (20% EPVG) in aqueous suspension. The bowel is distended with dark signal material after administration of the 20% EPVG contrast material and the bowel anatomy is better defined than without the contrast material. B) Coronal T2-weighted single shot non-fat saturation images of a 3 kg rabbit without (left image) and with (right image) enteric administration of 20% wt/wt encapsulated partial vacuum or gas hollow borosilicate particles (20% EPVG) in aqueous suspension. The bowel is distended with dark signal material after administration of the 20% EPVG contrast material and the bowel anatomy is better defined than without the contrast material.
Figure 2B:
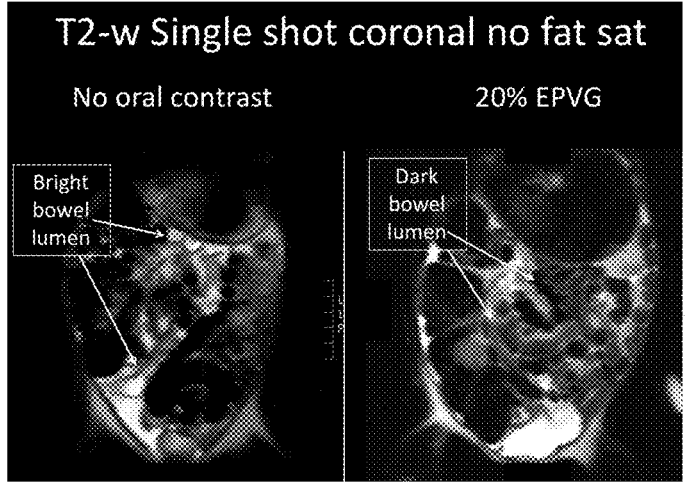
Figures 3A, 3B:
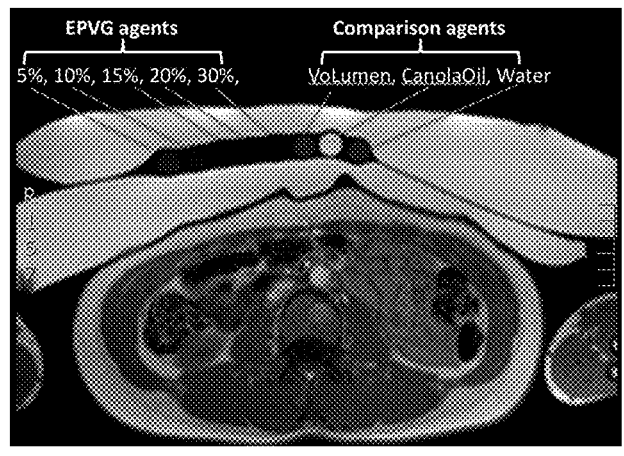
FIG. 3A-FIG. 3D shows exemplary 3T MR images of volunteer with overlying contrast material vials sandwiched between fat bags. Different concentrations of exemplary encapsulated partial vacuum or gas borosilicate glass microspheres with 5%, 10%, 15%, 20%, and 30% wt/wt suspension of specific gravity 0.45 hollow microspheres in aqueous media. The 15%, 20% and 30% wt/wt suspensions show low signal across all T1- and T2-weighted images, regardless of use of fat saturation. The 10% wt/wt suspensions show signals similar to or lower than that of non-fat soft tissues for all sequences. For comparison, the VoLumen and water vials show intermediate to low signal only on T1-weighted images. The canola oil only shows low signal when fat saturation is employed. VoLumen contrast material (Bracco, Italy) is 0.1% wt/wt barium sulfate suspension in aqueous media. A) T1-weighted gradient echo. B) T1-weighted gradient echo with fat saturation. C) T2-weighted single shot. D) T2-weighted turbo spin echo fat saturation.
Figure 3C:
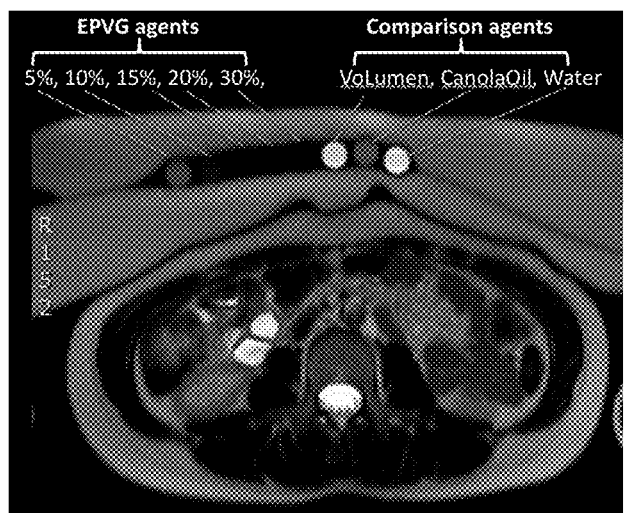
Figure 3D:
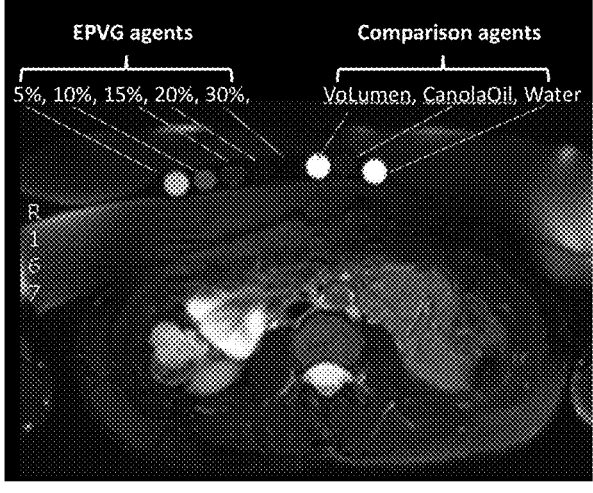
Figures 4A, 4B:
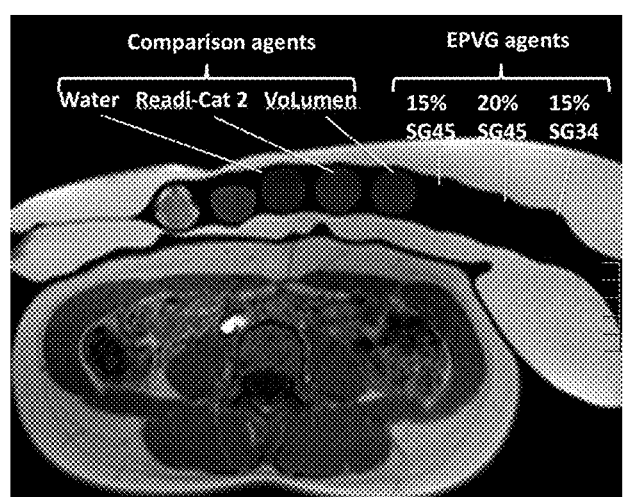
FIG. 4A-FIG. 4D shows exemplary 1.5 Tesla MR images of volunteer with overlying contrast material vials sandwiched between fat bags. Different concentrations of exemplary encapsulated partial vacuum or gas microspheres with 15%, 20%, and 15% wt/wt suspensions of specific gravity 0.45, 0.45, and 0.34 g/cc, respectively, encapsulated partial vacuum or gas borosilicate glass microspheres suspended in aqueous media. Each of the three exemplary encapsulated partial vacuum or gas microsphere suspensions show low signal across all T1- and T2-weighted images, regardless of use of fat saturation. For comparison, the Water, Readi-Cat 2, and VoLumen vials show intermediate to low signal on T1-weighted images and high signal on T2-weighted images. Readi-Cat 2 contrast material (Bracco, Italy) is composed of 2% wt/wt Barium Sulfate in aqueous suspension, and the VoLumen contrast material (Bracco, Italy) is 0.1% wt/wt barium sulfate suspension in aqueous media. SG45="true density 0.45". SG34="true density 0.34". A) T1-weighted gradient echo. B) T1-weighted gradient echo with fat saturation. C) T2-weighted single shot. D) T2-weighted turbo spin echo fat saturation.
Figures 4C, 4D:
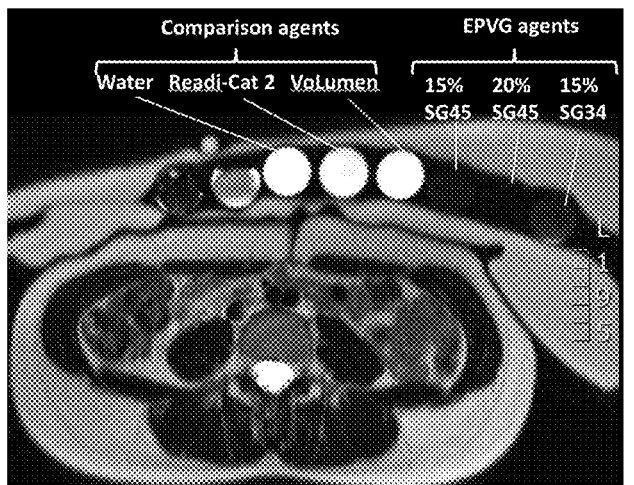
Figure 5A:
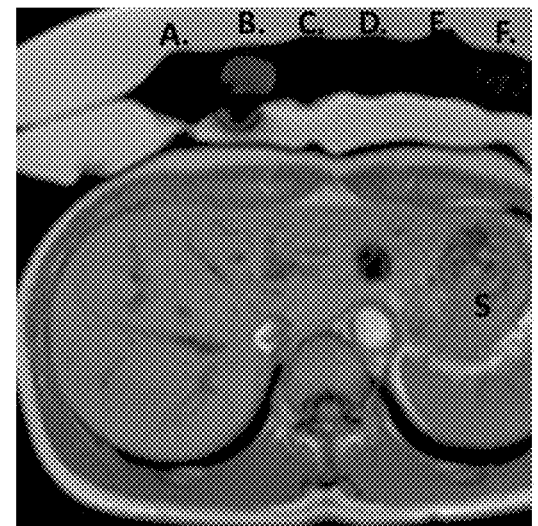
FIG. 5A-FIG. 5D shows exemplary 1.5 Tesla MR images of volunteer with overlying contrast material vials sandwiched between fat bags. Hollow borosilicate glass shell microspheres (A, C, D, E) each show low signal on both T1-weighted and T2-weighted images with minimal artifact on surrounding structures. Hollow phenolic shell (B) microspheres, which are porous to water, show signal similar to that of water on all sequences. Solid silica agent (F) showed low signal on T2 weighed images, but signal similar to water on T1-weighted fat saturation images. All contrast materials are in aqueous suspension at 20% wt/wt concentration. A. Hollow borosilicate microspheres of 17 micron diameter and true density 0.60 g/cc; B. Phenolic hollow microspheres of 5 to 130 micron diameter; 1 C. Hollow ceramic microspheres of 300-600 micron diameter; D. Hollow ceramic microspheres of 100 micron diameter; E) Hollow silver coated ceramic microspheres of 50 micron diameter; F Solid silica amorphous microspheres of 100 micron diameter. S=Stomach lumen which serves as reference for water signal. A) T1-weighted gradient echo. B) T1-weighted gradient echo with fat saturation. C) T2-weighted single shot. D) T2-weighted turbo spin echo fat saturation.
Figure 5B:
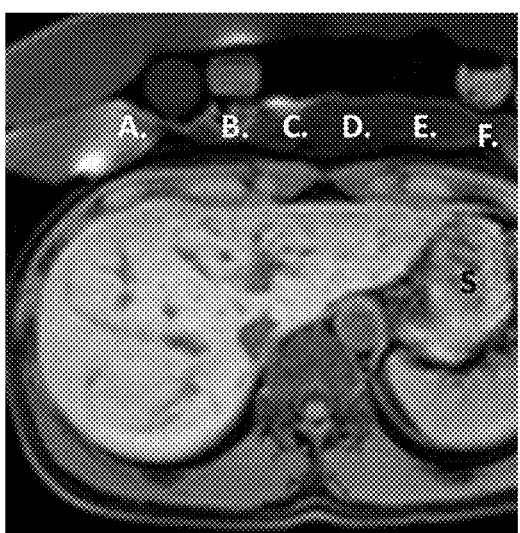
Figure 5C:
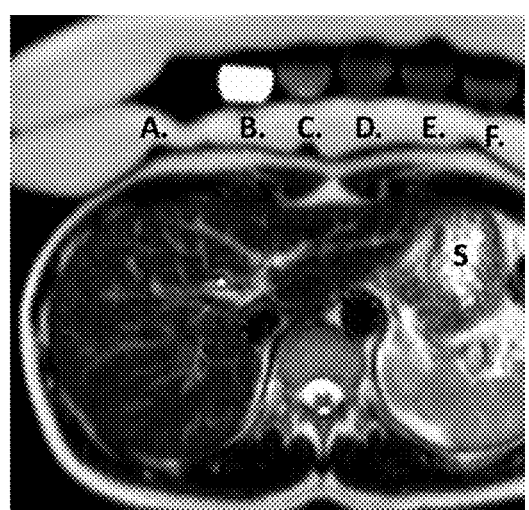
Figure 5D:
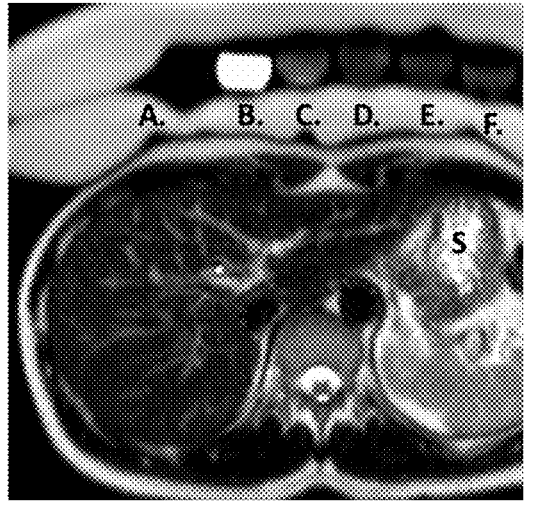

In vivo imaging experiments in rabbits and rats demonstrated that encapsulated gas or partial vacuum particle contrast medium formulation of the invention provides darkening of signal in the bowel with T1 and T2 weighted images. Shown are hollow borosilicate glass microspheres having true density 0.45 g/cc, at 20% wt/wt in aqueous suspension with 0.3% wt/wt xanthan gum. FIG. 2.

In vivo experiments showed excellent tolerance of mice, rats, rabbits, and dogs to repeat gastric gavage administrations of liquid suspensions of encapsulated gas or partial vacuum particle contrast media at doses up to 30 mL/kg, with no apparent health effects in up to 1 year of observation. Mice and rabbits were tested with 3M IM30K hollow borosilicate glass microspheres with true density 0.60 g/cc and mice with Potters Beads hollow borosilicate glass microspheres with true density 0.45 g/cc. Rats were tested with Potters Beads hollow borosilicate glass microspheres with true density 0.60 g/cc and 0.45 g/cc. Mice showed excellent tolerance to intratracheal administration and good tolerance with minimal to mild inflammation to subcutaneous and intraperitoneal administration of these same encapsulated gas or partial vacuum particle contrast media, showing that misadministration or extravasation of such agents outside the intestinal tract.

MR imaging of vials of exemplary encapsulated gas or partial vacuum particle contrast media at 1.5 T and 3 T scanners show consistent intermediate to low signal of the contrast media at T1-weighted and low signal at T2-weighted imaging, regardless of the use of fat saturation pulses (FIGS. 1, 3, 4, and 5).

Figures 6A, 6B, 6C:
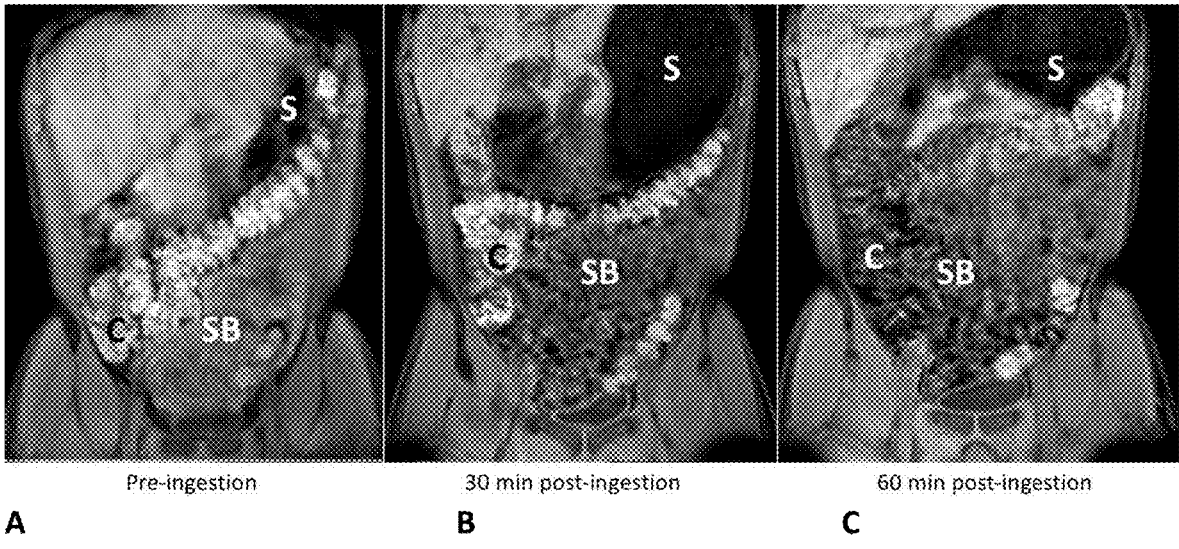
FIG. 6A-FIG. 6C show exemplary 1.5 Tesla T1-weighted Gradient Echo fat saturation coronal MR images of volunteer before (left image) and 30 and 60 minutes (middle and right images, respectively) after ingestion of 1200 mL of 9% wt/wt EPVG hollow borosilicate glass microspheres with true density 0.290 g/cc in aqueous suspension with xanthan gum, sorbitol and flavoring. Small bowel (SB) and proximal colon (C) show bright lumen signal which obscures the bowel wall delineation and may interfere with the ability to identify intrinsically bright T1 signal pathological processes such as hemorrhage or endometriomas, or to assess bowel wall enhancement if intravenous contrast were to be injected. At 30 minutes after ingestion of the EPVG oral contrast, the small bowel lumen is darkened and improves delineation of the small bowel wall. At 60 minutes after EPVG ingestion, the proximal colon lumen is also darkened and improves delineation of the colonic wall and folds. No detectable image artifact is seen involving the bowel wall around the bowel lumen filled with the exemplary enteric contrast agent of the invention. Stomach(S).
Figures 7A, 7B, 7C:
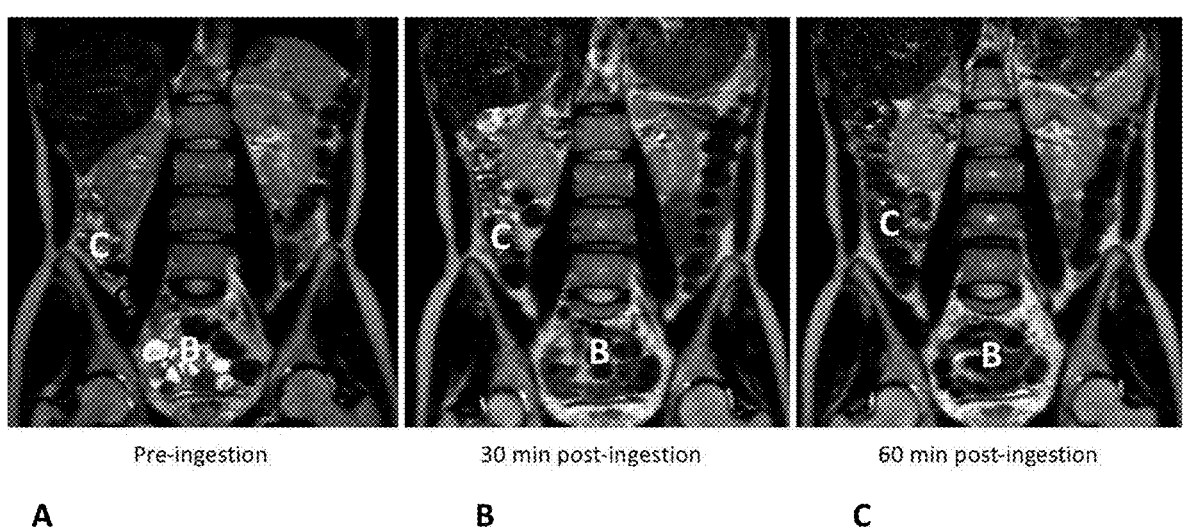
FIG. 7A-7C show exemplary 1.5 Tesla T2-weighted single-shot coronal MR images of volunteer before (left image) and 30 and 60 minutes (middle and right images, respectively) after ingestion of 9% wt/wt EPVG hollow borosilicate glass microspheres with true density 0.290 g/cc in aqueous suspension with xanthan gum, sorbitol and flavoring. Prior to EPVG oral contrast ingestion, the bowel lumen in the pelvis (B) and proximal colon (C) shows both markedly dark and bright signal, which can be disorienting. With 30 minutes after ingestion of 1200 mL of 9% EPVG oral contrast, the small bowel lumen darkens and, at 60 minutes after ingestion, the lumen of both the bowel in the pelvis and proximal colon becomes more uniformly dark, thereby allowing for more confident delineation of any bowel wall edema or wall thickening. No detectable image artifact is seen involving the bowel wall around the bowel lumen filled with the exemplary enteric contrast agent of the invention.
Figure 8:
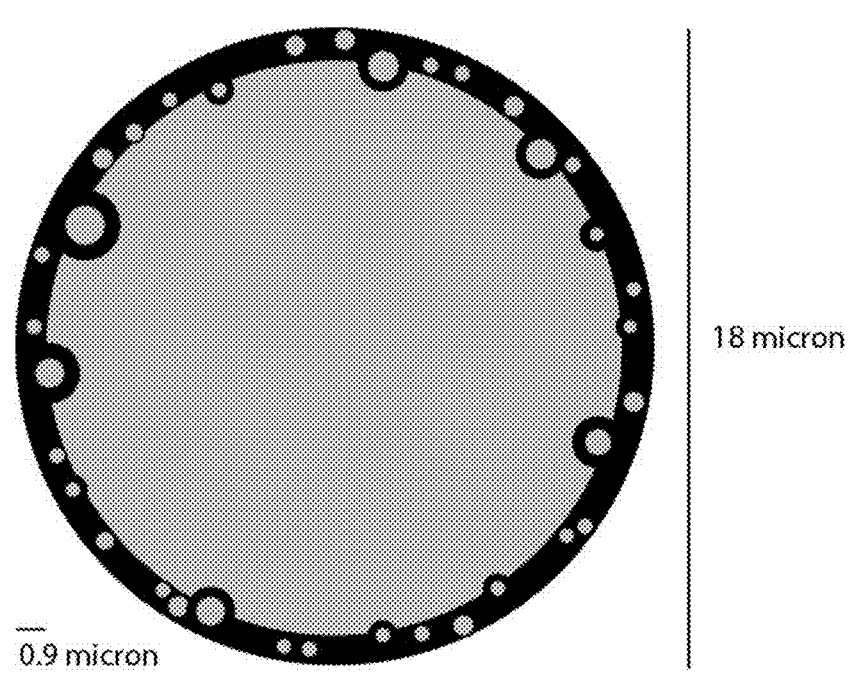
FIG. 8 shows an exemplary particle in an enteric contrast medium comprising a population of particles of the claimed invention. The particle comprises a central void defined by a solid shell maintaining within the central void an encapsulated gas or partial vacuum. Small imperfections of trapped gas and partial vacuum may exist in the shell material. The overall particle may have a dominant hollow space or may be subdivided by septations of shell material.

MR Imaging of exemplary formulations of exemplary encapsulated gas or partial vacuum particle contrast agent orally administered to a volunteer imaged on a 1.5 T scanner shows darkening of the bowel lumen on T1-weighted and T2-weighted imaging without noticeable image artifact (FIGS. 6 and 7).

The present invention has been illustrated by reference to various exemplary embodiments and examples. As will be apparent to those of skill in the art other embodiments and variations of this invention may be devised by others skilled in the art without departing from the true spirit and scope of the invention. The appended claims are to be construed to include all such embodiments and equivalent variations.

The disclosures of each and every patent, patent application, and publication cited herein are hereby incorporated herein by reference in their entirety.

22

What is claimed is:

1. An enteric contrast medium formulation which is formulated for oral delivery to a subject contemporaneous with a medical magnetic resonance (MR) imaging procedure performed on the gastrointestinal tract of said subject, said enteric contrast medium formulation comprising:
   a stable aqueous suspension of the enteric contrast medium, the enteric contrast medium comprising encapsulated partial vacuum or gas microspheres, wherein the enteric contrast medium is stably suspended in an aqueous pharmaceutically acceptable vehicle;
   the enteric contrast medium formulation comprising from 10% (wt/wt) to 50% (wt/wt) of the enteric contrast medium; and
   the aqueous pharmaceutically acceptable vehicle comprising 0.2 to 0.5% xanthan gum as a suspending agent maintaining the microspheres in suspension, the formulation having a viscosity of from 50 g/cm-sec to 2400 g/cm-sec; and
   wherein each hollow microsphere comprises a glass microparticle comprising a central void defined by a solid silicon dioxide shell, comprising silicon dioxide and maintaining within the central void an encapsulated gas or partial vacuum.

2. The enteric contrast medium formulation of claim 1, wherein said enteric contrast medium formulation is a unit dosage formulation comprising a diagnostically effective amount of said enteric contrast medium.

3. The enteric contrast medium formulation of claim 1, wherein said enteric contrast medium formulation is a unit dosage formulation of from about 800 mL to about 1500 mL per adult human dose, which may be divided into smaller containers such as 400 mL to 500 mL in volume.

4. The enteric contrast medium formulation of claim 1, wherein said enteric contrast medium formulation is a unit dosage formulation of from about 50 to about 100 mL in volume.

5. The enteric contrast medium formulation of claim 1, wherein enteric contrast medium formulation is a unit dosage formulation of from about 100 mL to about 800 mL in volume.

6. The enteric contrast medium formulation of claim 1, further comprising a suspension agent selected from guar gum, hydroxypropylmethyl cellulose, hydroxypropyl cellulose, polyvinyl pyrrolidone, alginates, polyethylene glycol chains, and sodium carboxylmethylcellulose.

7. The enteric contrast medium formulation of claim 1, wherein said enteric contrast medium formulation is a unit dosage formulation and it contains more than about 20 g of said encapsulated gas or partial vacuum microsphere.

8. The enteric contrast medium formulation of claim 1, wherein said aqueous pharmaceutically acceptable vehicle further comprises an additive to retard dehydration of said formulation in the bowel, a flavoring agent, a thickening agent, a flow agent, a pH buffer, a laxative, an osmolality-adjusting agent, or a combination thereof.

9. The enteric contrast medium formulation of claim 1, wherein said enteric contrast medium formulation produces low T1 signal similar to or lower than that of water.

10. The enteric contrast medium formulation of claim 1, wherein said enteric contrast medium formulation produces low T2 signal similar to or lower than that of skeletal muscle.

11. The enteric contrast medium formulation of claim 1, wherein the encapsulated gas or partial vacuum microsphere has a true density from about 0.15 to about 0.6.

12. The enteric contrast medium formulation of claim 1, wherein the encapsulated gas or partial vacuum microsphere has a mean diameter of from about 5 to about 60 micrometers.

13. The enteric contrast medium formulation of claim 1, wherein the encapsulated gas or partial vacuum microsphere has a mean diameter of from about 60 to about 200 micrometers.

14. The enteric contrast medium formulation of claim 1, wherein said enteric contrast medium is provided in powdered or other concentrated form to be mixed with water or other said acceptable pharmaceutical aqueous vehicle near the time of administration for MR imaging, together with instructions for preparing an administrable enteric contrast medium and, optionally, one or more device for administering said administrable enteric contrast medium to a subject.

15. The enteric contrast medium formulation of claim 1, wherein the encapsulated gas or partial vacuum microsphere makes up 5% or more of the weight of the formulation.

16. A kit comprising:

(a) a first vial or set of vials containing the enteric contrast medium of claim 1;

(b) a second vial containing a second contrast medium; and (c) directions for formulating said enteric contrast medium with or without said second contrast medium.

17. An enteric contrast medium formulation which is formulated for oral delivery to a subject contemporaneous with a MR imaging procedure performed on the abdomen or pelvis of said subject, said enteric contrast medium formulation comprising:

a stable aqueous suspension of the enteric contrast medium, the enteric contrast medium comprising encapsulated partial vacuum or gas microspheres, wherein the enteric contrast medium is stably suspended in an aqueous pharmaceutically acceptable vehicle;

the enteric contrast medium formulation comprising from 10% (wt/wt) to 50% (wt/wt) of the enteric contrast medium; and the aqueous pharmaceutically acceptable vehicle comprising 0.2 to 0.5% xanthan gum as a suspending agent maintaining the microspheres in suspension, the formulation having a viscosity of from 50 g/cm-sec to 2400 g/cm-sec; and wherein each hollow microsphere comprises a glass microparticle comprising a central void defined by a solid silicon dioxide shell, comprising silicon dioxide and maintaining within the central void an encapsulated gas or partial, suspended in an aqueous pharmaceutically acceptable vehicle component partial vacuum.

18. A method of acquiring a contrast enhanced MR image of a subject, said method comprising:

contemporaneously with performing a medical MR imaging procedure on said subject, administering to said subject a diagnostically effective amount of an enteric contrast medium formulation contemporaneous with a medical MR imaging procedure performed on said subject, wherein said enteric contrast medium formulation comprises:

a stable aqueous suspension of the enteric contrast medium, the enteric contrast medium comprising encapsulated partial vacuum or gas microspheres, wherein the enteric contrast medium is stably suspended in an aqueous pharmaceutically acceptable vehicle;

the enteric contrast medium formulation comprising from 10% (wt/wt) to 50% (wt/wt) of the enteric contrast medium; and the aqueous pharmaceutically acceptable vehicle comprising 0.2 to 0.5% xanthan gum as a suspending agent maintaining the microspheres in suspension, the formulation having a viscosity of from 50 g/cm-sec to 2400 g/cm-sec; and wherein each hollow microsphere comprises a glass microparticle comprising a central void defined by a solid silicon dioxide shell comprising, silicon dioxide and maintaining within the central void an encapsulated gas or partial vacuum; and performing a medical MR imaging procedure on said subject, thereby acquiring the contrast enhanced MR image of the subject.

19. The method according to claim 18, wherein MR k-space data are used to reconstruct said contrast enhanced MR image.

20. The method according to claim 18, wherein said contrast enhanced MR image is used to distinguish said enteric contrast medium formulation from other materials in the abdomen or the pelvis.

21. The method according to claim 18, wherein said contrast enhanced MR image is an image of a region selected from the abdomen and the pelvis of said subject.

22. The method of any of claim 18 wherein said enteric contrast medium formulation is administered to said subject by delivery through:

(a) a natural cavity selected from the mouth, vagina, bladder, rectum and urethra;

(b) a surgically created space selected from an ileal pouch, and a neobladder;

(c) a space created by injury selected from a fistula, sinus tract, and abscess; or (d) a medical device selected from a catheter, a tube, a reservoir, a pouch and a pump.

23. The method of claim 18, further comprising interpreting the contrast enhanced MR image of the subject and diagnosing said subject during image interpretation.

24. The method of claim 23, wherein said subject is evaluated for possible or known injury selected from a malignancy, inflammation, infection, and ischemia, and a combination thereof.

25. The method of claim 23, wherein said subject is evaluated for anatomical detail that involves the bowel or tissues adjacent to bowel.

26. An MRI image acquired by the method according to claim 18.

27. Two or more MR images according to claim 26, wherein said MR images are acquired during the same MR imaging procedure and at least one of said images is a T1-weighted image and at least one of said MR images is a T2-weighted image.

28. The MR image of claim 27, wherein the MR image is a T1-weighted image in which the signal in the lumen is darkened to below that of a member selected from soft tissue, bowel wall, or intravenous contrast enhanced tissue, on T1-weighted images, and the MR image is essentially free of T1-weighted image artifacts on the bowel wall or other gastrointestinal tract structures adjacent to the darkened bowel lumen.

29. The MR image of claim 27 wherein the T2-weighted image shows the signal in the gastrointestinal tract lumen is darkened to below that of a member selected from soft tissue, bowel wall, or edematous bowel wall, on T2-weighted images, and the MR image is essentially free of T2-weighted image artifacts on the bowel wall or other gastrointestinal tract structures adjacent to the darkened bowel lumen, and wherein the T1-weighted image shows the signal in the gastrointestinal tract lumen is darkened to below that of a member selected from soft tissue, bowel wall, or intravenous contrast enhanced tissue, on T1-weighted images, and the MR image is essentially free of T1-weighted image artifacts on the bowel wall or other gastrointestinal tract structures adjacent to the darkened bowel lumen.

30. The MR image of claim 26, wherein the MR image is a T2-weighted image in which the signal in the lumen is darkened to below that of a member selected from soft tissue, bowel wall, or edematous bowel wall, on T2-weighted images, and the MR image is essentially free of T2-weighted image artifacts on the bowel wall or other gastrointestinal tract structures adjacent to the darkened bowel lumen.

31. A MR image of at least a portion of the gastrointestinal tract of a subject, the MR image containing a first region of interest, which includes a lumen of a gastrointestinal tract structure and an interior void of said subject gastrointestinal tract structure defined by said lumen, the interior void having distributed therein suspended particles, wherein each particle comprises a hollow microsphere encapsulating gas or partial vacuum suspended in water containing 0.2 to 0.5% xanthan gum as a suspending agent maintaining the microspheres in suspension, the suspension having a viscosity of from 50 g/cm-sec to 2400 g/cm-sec;

the suspension comprising from 10% (wt/wt) to 50% (wt/wt) of the particles; and wherein each hollow microsphere comprises a glass microparticle comprising a central void defined by a solid silicon dioxide shell, comprising silicon dioxide and maintaining within the central void an encapsulated gas or partial, suspended in an aqueous pharmaceutically acceptable vehicle component partial vacuum.

* * * * *